(12) United States Patent
Akiyama et al.

(10) Patent No.: US 8,390,924 B2
(45) Date of Patent: Mar. 5, 2013

(54) ENDOSCOPE AND ENDOSCOPE APPARATUS

(75) Inventors: Daisuke Akiyama, Fuchu (JP); Takeshi Suga, Hino (JP); Satoshi Takekoshi, Hachioji (JP); Kazuhiro Gono, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/237,197

(22) Filed: Sep. 20, 2011

(65) Prior Publication Data

US 2012/0120487 A1 May 17, 2012

Related U.S. Application Data

(63) Continuation of application No. PCT/JP2011/057358, filed on Mar. 25, 2011.

(30) Foreign Application Priority Data

May 19, 2010 (JP) ................................ 2010-115563

(51) Int. Cl.
G02B 21/06 (2006.01)
G02B 23/26 (2006.01)
(52) U.S. Cl. ......... 359/386; 359/389; 385/117; 600/178
(58) Field of Classification Search .................. 359/385, 359/386, 389; 385/116, 117; 600/160, 178
See application file for complete search history.

(56) References Cited

U.S. PATENT DOCUMENTS

| | | | | |
|---|---|---|---|---|
| 4,870,950 A | * | 10/1989 | Kanbara et al. | 600/109 |
| 5,406,938 A | * | 4/1995 | Mersch et al. | 600/138 |
| 7,515,952 B2 | * | 4/2009 | Balas et al. | 600/476 |
| 2002/0007123 A1 | | 1/2002 | Balas | |
| 2002/0161282 A1 | * | 10/2002 | Fulghum | 600/160 |
| 2003/0040668 A1 | | 2/2003 | Kaneko et al. | |
| 2005/0159641 A1 | * | 7/2005 | Kanai | 600/101 |
| 2007/0177009 A1 | | 8/2007 | Bayer et al. | |
| 2008/0275298 A1 | * | 11/2008 | Ratnakar | 600/109 |
| 2009/0131800 A1 | * | 5/2009 | Liang | 600/476 |
| 2009/0225156 A1 | * | 9/2009 | Akiyama et al. | 348/68 |
| 2010/0005850 A1 | | 1/2010 | Gono et al. | |
| 2010/0026785 A1 | * | 2/2010 | Soto-Thompson et al. | 348/47 |

(Continued)

FOREIGN PATENT DOCUMENTS

| | | |
|---|---|---|
| EP | 0 586 162 A1 | 3/1994 |
| EP | 2 057 936 A1 | 5/2009 |

(Continued)

OTHER PUBLICATIONS

European Search Report dated May 8, 2012 from corresponding European Patent Application No. EP 11 78 3329.3.

*Primary Examiner* — Frank Font
(74) *Attorney, Agent, or Firm* — Scully Scott Murphy & Presser, PC

(57) ABSTRACT

An endoscope includes: a first illumination optical system which emits illuminating light in a first linear polarization direction to an object from a distal end face of an insertion portion; and a first objective optical system which allows return light from the object to enter through an objective window provided in the distal end face; wherein the first illumination optical system and the first objective optical system are placed in a positional relationship such that on the distal end face, a line segment connecting an optical axis of the first illumination optical system and an optical axis of the first objective optical system is parallel or perpendicular to a polarization direction which results when the illuminating light emitted from the first illumination optical system is projected to the distal end face, and no polarizing element is provided between the object and the objective window.

7 Claims, 10 Drawing Sheets

U.S. PATENT DOCUMENTS

| | | |
|---|---|---|
| 2010/0079588 A1 | 4/2010 | Murooka et al. |
| 2010/0102211 A1 | 4/2010 | Murooka et al. |
| 2010/0208275 A1* | 8/2010 | Babayoff .................... 356/610 |

FOREIGN PATENT DOCUMENTS

| | | |
|---|---|---|
| JP | 2003-047588 | 2/2003 |
| JP | 2003-527915 | 9/2003 |
| JP | 2007143580 A * | 6/2007 |
| JP | 2007-282965 | 11/2007 |
| JP | 2009-525830 | 7/2009 |
| WO | WO 01/72214 A1 | 10/2001 |
| WO | WO 2007/092636 A2 | 8/2007 |

* cited by examiner

ENDOSCOPE AND ENDOSCOPE APPARATUS

CROSS REFERENCE TO RELATED APPLICATION

This application is a continuation application of PCT/JP2011/057358 filed on Mar. 25, 2011 and claims benefit of Japanese Application No. 2010-115563 filed in Japan on May 19, 2010, the entire contents of which are incorporated herein by this reference.

BACKGROUND OF THE INVENTION

1. Field of the Invention

The present invention relates to an endoscope and an endoscope apparatus, and more particularly, to an endoscope and endoscope apparatus used for polarization imaging.

2. Description of the Related Art

Conventionally, techniques for imaging (polarization imaging) using polarization characteristics of light have been proposed in various fields including the industrial and medical fields.

For example, U.S. Pat. No. 5,406,938 proposes an endoscope which includes a component (polarizer) adapted to cause illuminating light emitted to an object and light from the illuminating light reflected off the object to differ from each other in polarization characteristics.

Also, for example, Japanese Patent Application Laid-Open Publication No. 2007-282965 proposes an endoscopic imaging apparatus which identifies a specific site in a living body using unique spectral absorption characteristics of near-infrared light at 1200 nm or longer, including a polarizer provided in each of an illumination optical system and an image pickup optical system, wherein a polarization direction of light entering the polarizer in the image pickup optical system after being reflected by the living body is set to be orthogonal to a polarization direction of the polarizer in the image pickup optical system.

SUMMARY OF THE INVENTION

An endoscope according to one aspect of the present invention includes: a first illumination optical system configured to emit illuminating light in a first linear polarization direction to an object from a distal end face of an insertion portion; and a first objective optical system configured to allow return light from the object illuminated by the illuminating light to enter through an objective window provided in the distal end face; wherein the first illumination optical system and the first objective optical system are placed in a positional relationship such that on the distal end face, a line segment connecting an optical axis of the first illumination optical system and an optical axis of the first objective optical system is parallel or perpendicular to a polarization direction which results when the illuminating light emitted from the first illumination optical system is projected to the distal end face, and no polarizing element is provided between the object and the objective window.

An endoscope according to another aspect of the present invention includes: an endoscope insertion portion which includes an illumination optical system configured to emit illuminating light to an object from a distal end face of the insertion portion, and an objective optical system configured to allow return light from the object illuminated by the illuminating light to enter through the distal end face; and an endoscope cap which includes a cap portion having a shape attachable to a distal end portion of the endoscope insertion portion, a bottom face placed facing the distal end face of the distal end portion when the cap portion is attached to the endoscope insertion portion, an illuminating window provided in the bottom face and configured to polarize the illuminating light emitted from the illumination optical system in a predetermined linear polarization direction and emit the polarized illuminating light to the object, an objective window provided in the bottom face so as to be placed in a position between the object and the objective optical system which allows the return light from the object to be emitted to the objective optical system when the cap portion is attached to the endoscope insertion portion, wherein the illuminating window and the objective window are placed in a positional relationship such that in the bottom face, a line segment connecting an optical axis of the illuminating window and an optical axis of the objective window is parallel or perpendicular to a polarization direction which results when the illuminating light emitted through the illuminating window is projected to the bottom face, and no polarizing element is provided between the object and the objective window.

An endoscope apparatus according to one aspect of the present invention includes: an endoscope; a light source apparatus adapted to supply the endoscope with light having no polarization characteristics; and a processor adapted to generate an observation image according to an optical image of an object obtained by the endoscope, wherein the endoscope includes a first illumination optical system configured to emit illuminating light in a first linear polarization direction to the object from a distal end face of an insertion portion, and a first objective optical system configured to allow return light from the object illuminated by the illuminating light to enter through an objective window provided in the distal end face, the first illumination optical system and the first objective optical system are placed in a positional relationship such that on the distal end face, a line segment connecting an optical axis of the first illumination optical system and an optical axis of the first objective optical system is parallel or perpendicular to a polarization direction which results when the illuminating light emitted from the first illumination optical system is projected to the distal end face, and no polarizing element is provided between the object and the objective window.

An endoscope apparatus according to another aspect of the present invention includes: an endoscope; a light source apparatus adapted to supply the endoscope with light having no polarization characteristics; and a processor adapted to generate an observation image according to an optical image of an object obtained by the endoscope, wherein the endoscope includes an endoscope insertion portion which includes an illumination optical system configured to emit illuminating light to the object from a distal end face of the insertion portion and an objective optical system configured to allow return light from the object illuminated by the illuminating light to enter through the distal end face, and an endoscope cap which includes a cap portion having a shape attachable to a distal end portion of the endoscope insertion portion, a bottom face placed facing the distal end face of the distal end portion when the cap portion is attached to the endoscope insertion portion, an illuminating window provided in the bottom face and configured to polarize the illuminating light emitted from the illumination optical system in a predetermined linear polarization direction and emit the polarized illuminating light to the object, and an objective window provided in the bottom face so as to be placed in a position between the object and the objective optical system as to allow the return light from the object to be emitted to the objective optical system when the cap portion is attached to the endoscope insertion portion, the illuminating window and the objective window are placed in a positional relationship such that in the bottom face, a line segment connecting an optical axis of the illuminating window and an optical axis of the objective window is parallel or perpendicular to a polarization direction which results when the illuminating light emitted through the illuminating window is projected to the bottom face, and no polarizing element is provided between the object and the objective window.

DETAILED DESCRIPTION OF THE PREFERRED EMBODIMENTS

Embodiments of the present invention will be described below with reference to the drawings.

First Embodiment

FIGS. 1 to 6 concern a first embodiment of the present invention.

Figure 1:
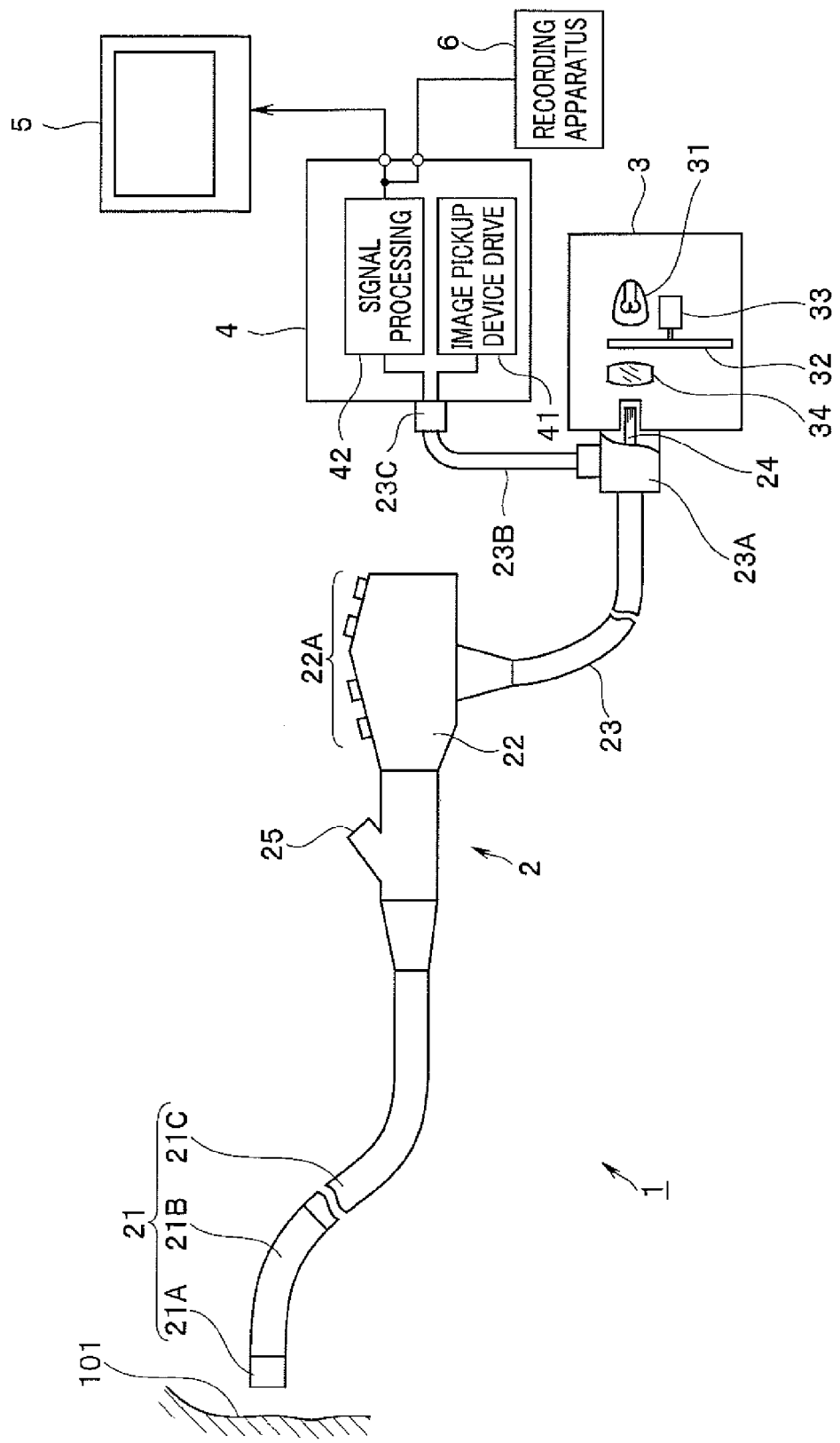
FIG. 1 is a diagram showing an exemplary configuration of principal part of an endoscope apparatus equipped with an endoscope according to an embodiment of the present invention.

As shown in FIG. 1, an endoscope apparatus 1 includes an endoscope 2 adapted to pick up optical images of an object 101 which is a living tissue and output an image pickup signal, a light source apparatus 3 adapted to supply the endoscope 2 with illuminating light for illuminating the object 101, a processor 4 adapted to generate and output a video signal according to the image pickup signal outputted from the endoscope 2, a monitor 5 adapted to display images according to the video signal outputted from the processor 4, and a recording apparatus 6 capable of recording the video signal outputted from the processor 4.

The endoscope 2 includes an insertion portion 21 inserted into a body cavity, an operation portion 22 provided on a rear end side of the insertion portion 21, and a universal code 23 extended from a lateral portion of the operation portion 22. Also, the endoscope 2 can be detachably connected to the light source apparatus 3 via a connector 23A provided in an end portion of the universal code 23. Furthermore, the endoscope 2 can be detachably connected to the processor 4 via a connector 23C provided in an end portion of a signal cable 23B extending from the connector 23A.

The insertion portion 21 of the endoscope 2 includes a rigid, distal end portion 21A, a bending portion 21B structured to be bendable and provided at a rear end of the distal end portion 21A, and a flexible tubular portion 21C extending from a rear end of the bending portion 21B to a front end of the operation portion 22.

A light guide 24 used to transmit the illuminating light supplied from the light source apparatus 3 to the distal end portion 21A is contained in that portion of the endoscope 2 which runs from the connector 23A to the distal end portion 21A.

Also, the insertion portion 21 of the endoscope 2 contains a treatment instrument channel (not shown) serving as a conduit which allows insertion of an elongated treatment instrument. The treatment instrument channel is communicated with a treatment instrument insertion port 25 which is an opening formed near the operation portion 22 and with a treatment instrument extrusion port (treatment instrument extrusion port 223 described later) which is an opening formed in a distal end face of the distal end portion 21A.

Now, a specific example of internal configuration of the distal end portion 21A will be described.

Figure 2:
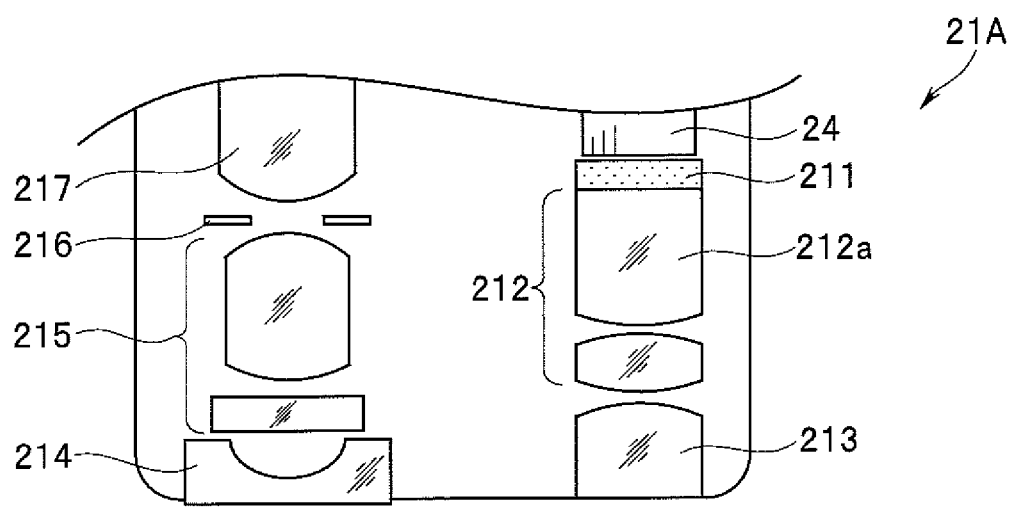
FIG. 2 is a diagram showing a concrete configuration example of a distal end portion of an endoscope according to a first embodiment.

As shown in FIG. 2, inside the distal end portion 21A, an exit-side end face of the light guide 24 is placed and components of an illumination optical system are provided, including a linear polarizer 211, an illumination lens group 212, and an illuminating window 213. Also, as shown in FIG. 2, the distal end portion 21A has a component arrangement such that the illuminating light emitted from the exit-side end face of the light guide 24 will pass through the linear polarizer 211, the illumination lens group 212, and the illuminating window 213 in this order.

The linear polarizer 211 is configured to be able to align a polarization direction of the illuminating light emitted from the exit-side end face of the light guide 24, and thereby generate illuminating light of a predetermined polarization direction (P-polarization), and emit the illuminating light to the illumination lens group 212.

The illumination lens group 212 is made up of multiple lenses including at least a rod lens 212a and configured to be able to transmit the illuminating light passing through the linear polarizer 211 to the illuminating window 213 and emit the illuminating light through the illuminating window 213.

The illuminating window 213 is made of a convex lens and configured to be able to emit the illuminating light passing through the illumination lens group 212 to the object 101.

According to the present embodiment, the linear polarizer 211 may be placed not only on an entrance side of the rod lens 212a, but also on an exit side of the rod lens 212a.

As shown in FIG. 2, when the linear polarizer 211 is placed on the entrance side of the rod lens 212a, design flexibility of the illumination lens group 212 can be increased. On the other hand, when the linear polarizer 211 is placed on the exit side of the rod lens 212a, changes in the polarization direction resulting from passage through the rod lens 212a can be reduced, which makes it easier to emit the illuminating light to the object 101 with the polarization direction (predetermined polarization direction) upon the passage through the linear polarizer 211 maintained.

On the other hand, as shown in FIG. 2, inside the distal end portion 21A, components of an objective optical system are provided, including an objective window 214, a first objective lens group 215, an objective diaphragm 216, and a second objective lens group 217. Also, as shown in FIG. 2, the distal end portion 21A has a component arrangement such that return light from the object 101 will pass through the objective window 214, the first objective lens group 215, the objective diaphragm 216, and the second objective lens group 217 in this order.

The objective window 214 is made of a concave lens and configured to be able to emit the return light from the object 101 to the first objective lens group 215.

The first objective lens group 215 is configured to be able to emit the return light passing through the objective window 214 to the objective diaphragm 216.

The objective diaphragm 216 is configured to be able to limit (reduce) quantity of the return light passing through the first objective lens group 215 and thereby emit the return light to the second objective lens group 217.

The second objective lens group 217 is configured to be able to collect and focus the return light passing through the objective diaphragm 216 on an image pickup surface of an image pickup device (not shown) placed on an exit side of the second objective lens group 217. Then, an optical image of the return light collected and focused by the second objective lens group 217 is picked up by the image pickup device and outputted to the processor 4 as an image pickup signal.

Next, a specific example of layout locations of components placed on the distal end face of the distal end portion 21A will be described.

Figure 3:
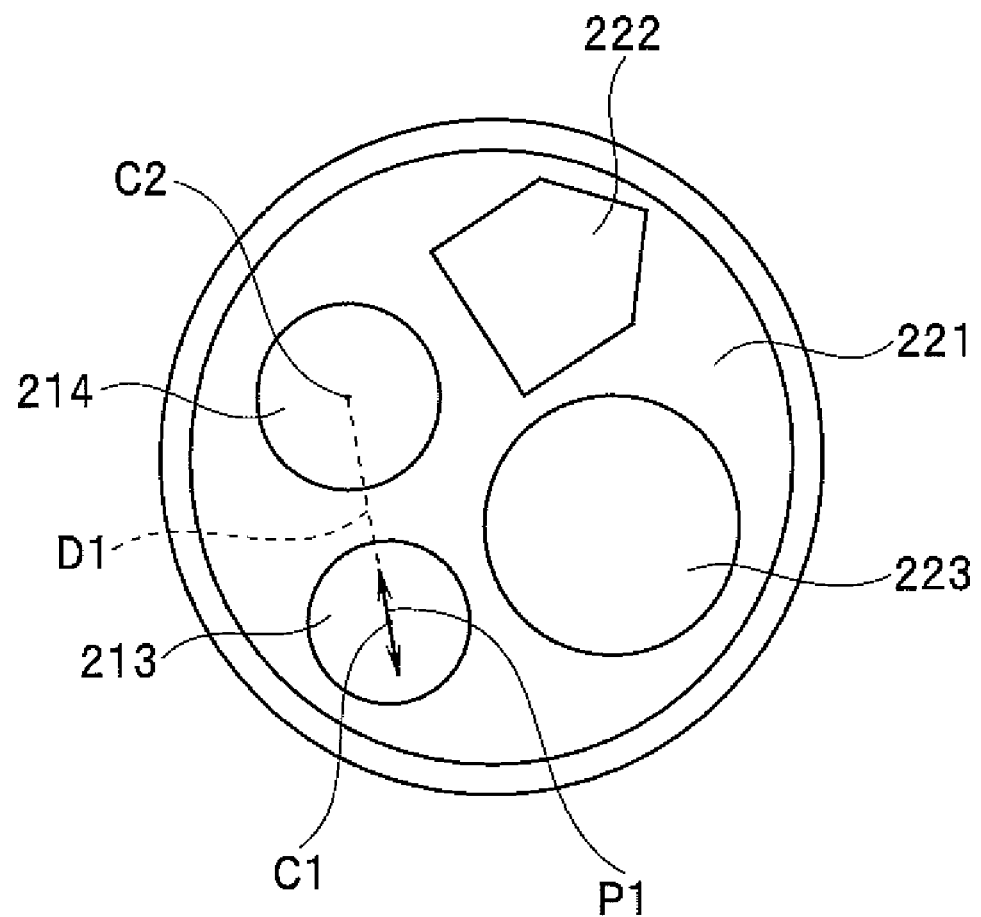
FIG. 3 is a diagram showing a component arrangement of principal part provided on a distal end face of the distal end portion of the endoscope according to the first embodiment.

As shown in FIG. 3, the distal end face 221 of the distal end portion 21A is provided with (an exit-side face of) the illuminating window 213, (an entrance-side face of) the objective window 214, a nozzle 222, and a treatment instrument extrusion port 223, where the nozzle 222 has a spout (not shown) placed so as to eject cleaning gas and fluid flowing through an air/water supply conduit (not shown) contained in the insertion portion 21 toward (the entrance-side face of) the objective window 214 and the treatment instrument extrusion port 223 is formed as an opening communicated with a treatment instrument channel (not shown) contained in the insertion portion 21.

As shown in FIG. 3, if it is assumed that an optical axis of the illuminating window 213 (or the illumination optical system including the illuminating window 213) passes through a center C1 of the illuminating window 213 and that an optical axis of the objective window 214 (or the objective optical system including the objective window 214) passes through a center C2 of the objective window 214, the illuminating window 213 and objective window 214 according to the present embodiment are placed in a positional relationship such that in a plane (distal end face 221) which includes the optical axis of the illuminating window 213 and the optical axis of the objective window 214, a line segment (broken line D1 in FIG. 3) connecting the two optical axes (center C1 and center C2 in FIG. 3) is parallel to a line segment (line segment P1 in FIG. 3) corresponding to the polarization direction of the illuminating light emitted through the illuminating window 213 and projected to the distal end face 221.

The bending portion 21B is equipped inside with a bendable structure such as bending pieces or a wire (none is shown) and structured to be bendable in a desired direction according to operation of a bending knob (not shown) provided in the operation portion 22.

The operation portion 22 is shaped grippable with any of the hands and equipped with a scope switch group 22A placed in such a position as to be used to give operation commands to the processor 4 and the like with the operation portion 22 gripped with the hand.

The signal cable 23B and connector 23C of the universal code 23 contain multiple signal lines used to transmit/receive various signals between the endoscope 2 and the processor 4.

The light source apparatus 3 includes a lamp 31 adapted to give off white color light having no polarization characteristics, a rotating filter 32 on which the light given off by the lamp 31 is incident, a motor 33 adapted to supply a driving force for rotating the rotating filter 32 in a predetermined direction at constant speed, and a condenser lens 34 adapted to condense the light passing through the rotating filter 32 and supply the condensed light to the light guide 24.

The rotating filter 32 is shaped as a disk centered on a rotating shaft. Along a peripheral edge of the disk shape, the rotating filter 32 has an R filter adapted to transmit light in a red wavelength region, a G filter adapted to transmit light in a green wavelength region, and a B filter adapted to transmit light in a blue wavelength region.

That is, with the configuration of the light source apparatus 3, when the driving force generated by the motor 33 is supplied to the rotating shaft of the rotating filter 32, the R filter, the G filter, and the B filter are inserted sequentially and successively in an optical axis of the lamp 31 and red light, green light, and blue light are supplied as frame-sequential illuminating light to the light guide 24 (through the condenser lens 34).

The processor 4 contains an image pickup device drive circuit 41 adapted to drive an image pickup device (not shown) provided in the distal end portion 21A and a signal processing circuit 42 adapted to generate and output a video signal by performing signal processing on an image pickup signal outputted from the image pickup device.

Next, operation of the present embodiment will be described.

First, a surgeon or the like connects various parts of the endoscope apparatus 1 as shown in FIG. 1 and powers on the various parts. Then, the surgeon or the like inserts the insertion portion 21 into the body of an examinee and brings the distal end portion 21A close to the object 101 in a desired observation region.

Consequently, illuminating light with substantially no polarization characteristics is emitted from the distal end portion 21A to illuminate the object 101. Then, internally scattered light produced by being transmitted through a surface of the object 101 and scattered in inner part near the surface layer and surface-reflected light produced by reflecting off the surface of the object 101 enter the objective window 214 as return light. Accordingly, on the image pickup surface of the image pickup device placed on the exit side of the second objective lens group 217, respective optical images of the object 101 are formed by the internally scattered light and the surface-reflected light and integrated into a single optical image.

That is, image pickup signals are obtained by picking up an optical image of the object 101 resulting from red internally scattered light and surface-reflected light, an optical image of the object 101 resulting from green internally scattered light and surface-reflected light, and an optical image of the object 101 resulting from blue internally scattered light and surface-reflected light, and the image pickup signals are outputted to the processor 4.

Subsequently, the signal processing circuit 42 of the processor 4 generates a video signal by performing signal processing on the image pickup signals outputted from the endoscope 2 and outputs the video signal to the monitor 5 and the recording apparatus 6. Consequently, images of substantially the same coloration (white light images) as in the case of observations made with the unaided eye are displayed on the monitor 5 and recorded on the recording apparatus 6 based on the video signal.

In the following description, a central axis of the distal end portion 21A corresponding to an insertion axis direction of the insertion portion 21 is set as a reference line and an incident angle with respect to the central axis when the illuminating light emitted through the illuminating window 213 enters the object 101 is set to θ.

Figure 5A:
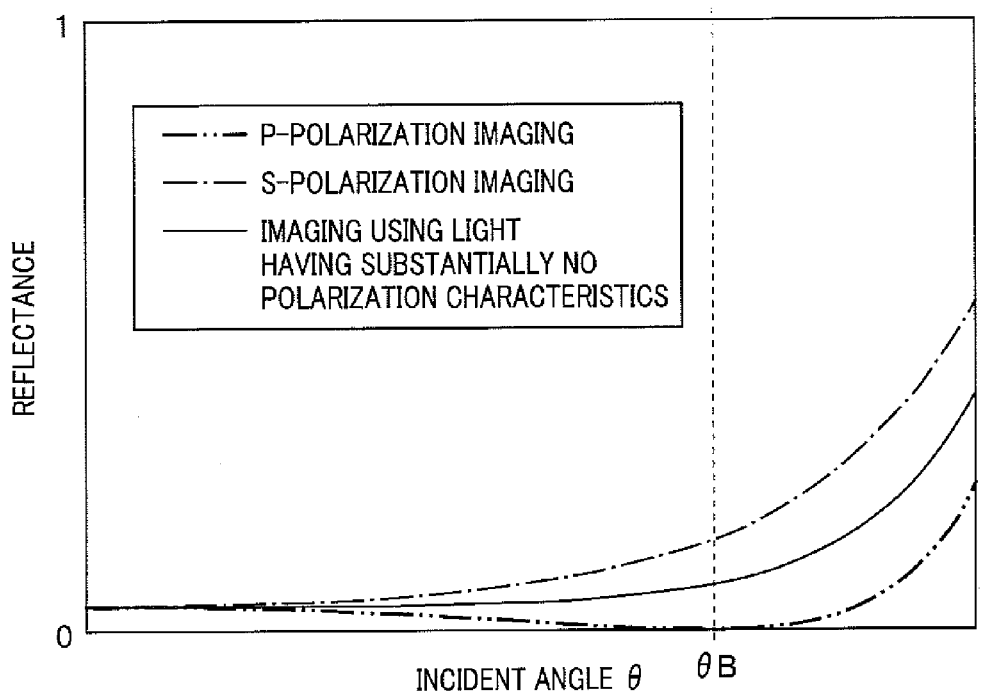
FIG. 5A is a diagram showing an example of a relationship between an incident angle of illuminating light entering a living tissue and reflectance of the illuminating light on a surface of the living tissue.
Figure 5B:
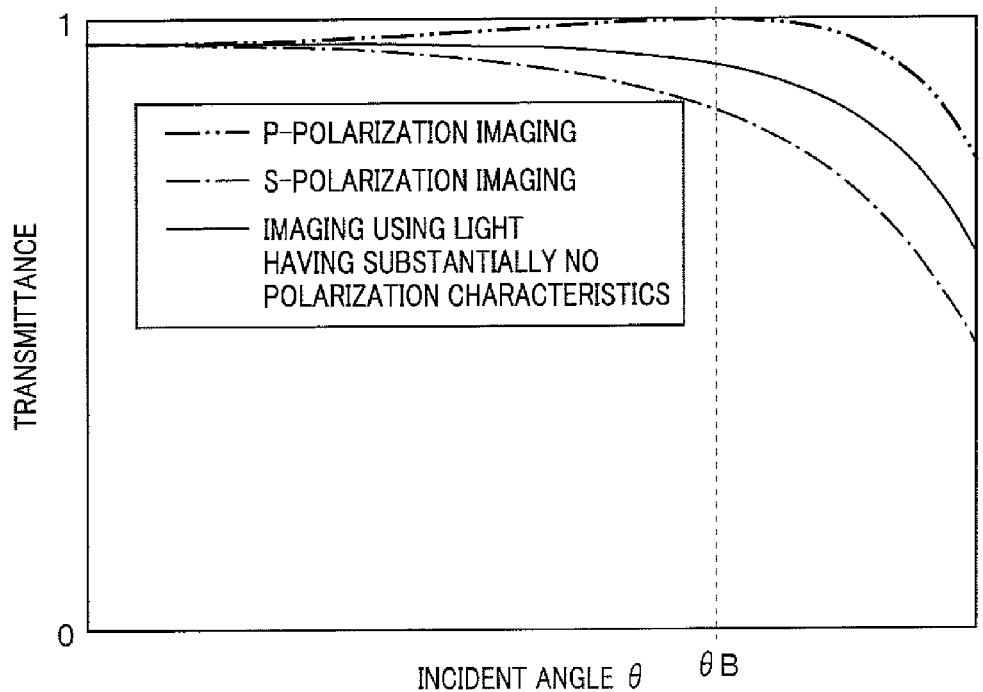
FIG. 5B is a diagram showing an example of a relationship between an incident angle of illuminating light entering a living tissue and transmittance of the illuminating light on the surface of the living tissue.

Reflectance and transmittance on the surface of the object 101 which is a living tissue have a relationship shown in FIGS. 5A and 5B with the incident angle θ set as described above, where the relationship is based on Fresnel's formula. In other words, FIGS. 5A and 5B show that angular characteristics of both reflectance and transmittance on the surface of the object 101 which is a living tissue vary depending on whether or not the illuminating light emitted through the illuminating window 213 has polarization characteristics as well as on a difference of the polarization direction of the illuminating light.

On the other hand, according to the present embodiment, in a plane (distal end face 221) which includes the optical axis of the illuminating window 213 and the optical axis of the objective window 214, a line segment (broken line D1 in FIG. 3) connecting the two optical axes (center C1 and center C2 in FIG. 3) and a line segment (line segment P1 in FIG. 3) corresponding to the polarization direction of the illuminating light emitted through the illuminating window 213 and projected to the distal end face 221 are placed in such a positional relationship as to be parallel to each other. That is, according to the present embodiment, since the illuminating light emitted to the object 101 through the illuminating window 213 has polarization characteristics of P-polarization whereby the illuminating light is parallel to an incident plane of the illuminating light, angular characteristics of reflectance and transmittance indicated as "P-polarization imaging" in FIGS. 5A and 5B are applied.

Figure 4:
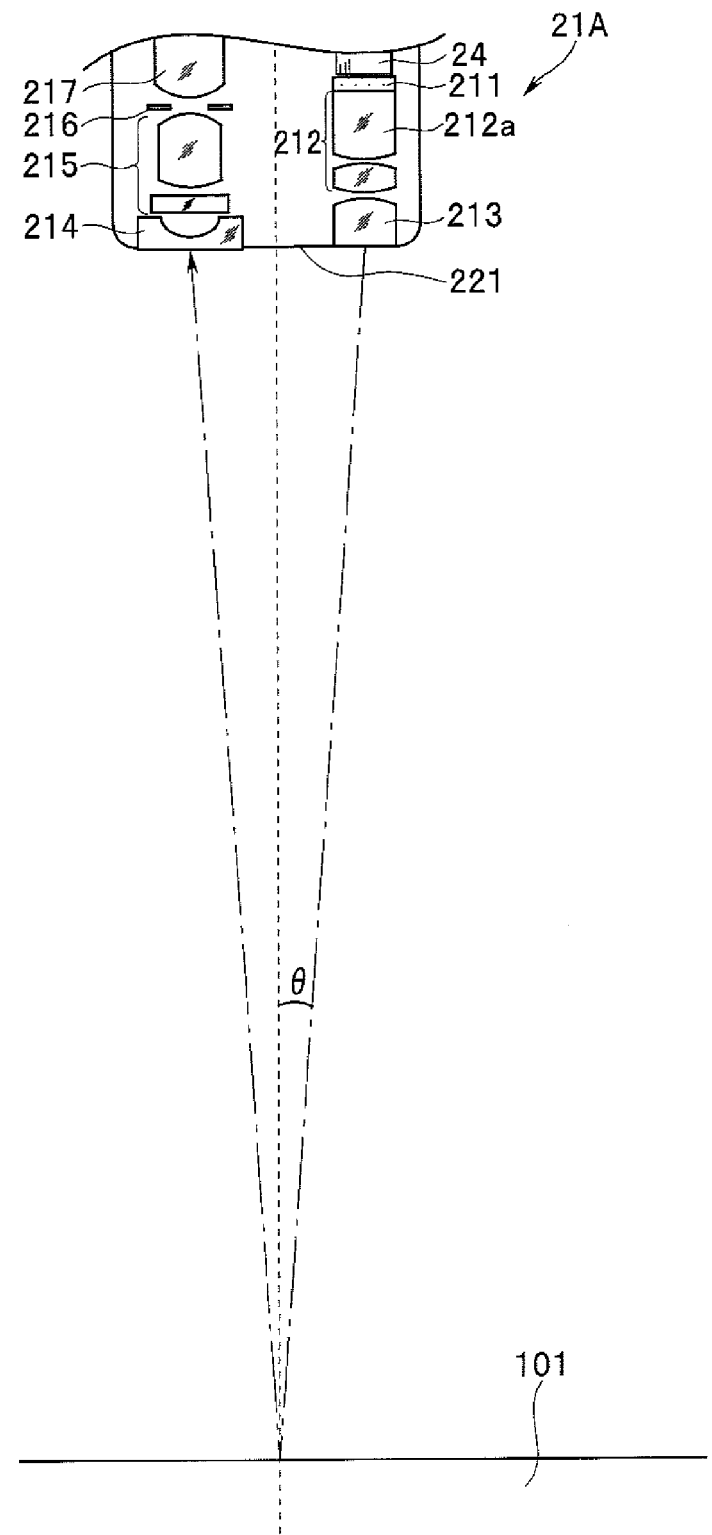
FIG. 4 is a diagram showing an example of a positional relationship between an object and the distal end portion of the endoscope in the case of far point observation.

For example, as shown in FIG. 4, if there is a large distance between the distal end face 221 of the distal end portion 21A and the surface of the object 101 (in the case of far point observation), the incident angle θ is relatively small. Therefore, in the case of far point observation, as shown in FIGS. 5A and 5B, both reflectance and transmittance of the illuminating light emitted through the illuminating window 213, as measured on the surface of the object 101, are substantially the same between when there are polarization characteristics and when there are not polarization characteristics as well as between different polarization directions. That is, in the case of far point observation, an intensity ratio between an optical image resulting from internally scattered light produced by being transmitted through the surface of the object 101 and scattered in inner part near the surface layer and an optical image resulting from surface-reflected light produced by reflecting off the surface of the object 101 is substantially the same between when the object 101 is illuminated by illuminating light having substantially no polarization characteristics and when the object 101 is illuminated by the illuminating light emitted through the illuminating window 213 according to the present embodiment.

Thus, according to the present embodiment, when there is a relatively large distance between the distal end face 221 of the distal end portion 21A and the surface of the object 101 (in the case of far point observation), observations can be made by watching substantially the same images as those obtained when the object 101 is illuminated by illuminating light having substantially no polarization characteristics.

Figure 6:
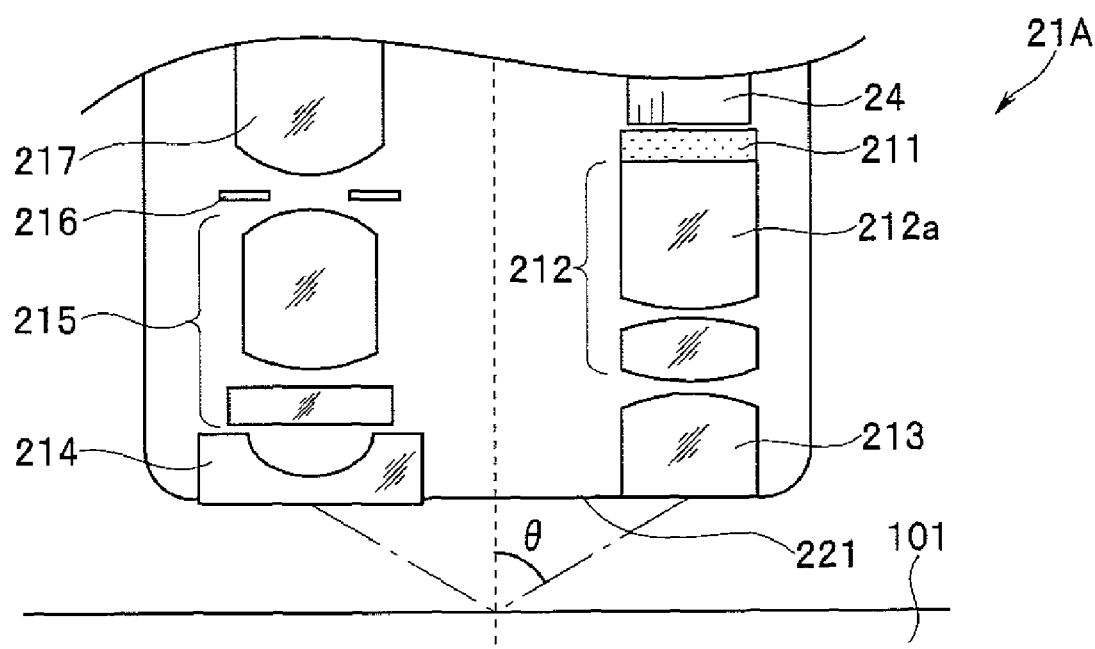
FIG. 6 is a diagram showing an example of a positional relationship between an object and the distal end portion of the endoscope in the case of near point observation.

On the other hand, in the case of far point observation, the surgeon or the like operates the insertion portion 21 by watching white light images displayed on the monitor 5 and thereby brings the distal end face 221 of the distal end portion 21A close to the surface of the object 101 until a positional relationship such as shown in FIG. 6 is established.

When the distal end face 221 of the distal end portion 21A is brought close to the surface of the object 101 shown in FIG. 6 (in the case of near point observation), the incident angle θ becomes relatively large.

Specifically, for example, when the distance between the distal end face 221 of the distal end portion 21A and the surface of the object 101 is reduced to a few mm to 10 mm, the incident angle θ can be set close to the Brewster angle θB. In bringing the incident angle θ close to the Brewster angle θB, the distance between the distal end face 221 of the distal end portion 21A and the surface of the object 101 appropriately varies depending on length of the line segment connecting the center C1 and the center C2 (distance between the center C1 and the center C2).

When the object 101 is illuminated by illuminating light having polarization characteristics of P-polarization with the incident angle θ set close to the Brewster angle θB, internally scattered light produced by being transmitted through the surface of the object 101 and scattered in inner part near the surface layer enters the objective window 214 as return light having a higher intensity than when the object 101 is illuminated by illuminating light having substantially no polarization characteristics, as shown in FIG. 5B. On the other hand, when the object 101 is illuminated by illuminating light having polarization characteristics of P-polarization with the incident angle θ set close to the Brewster angle θB, intensity of surface-reflected light produced by reflecting off the surface of the object 101 can be reduced to almost 0 (or to 0), and thus little (or none) of the surface-reflected light enters the objective window 214 as shown in FIG. 5A. Accordingly, on the image pickup surface of the image pickup device placed on the exit side of the second objective lens group 217, an optical image of the object 101 resulting from the internally scattered light is formed with the surface-reflected light removed almost completely (or completely).

That is, when the distance between the distal end face 221 of the distal end portion 21A and the surface of the object 101 is reduced until the incident angle θ is brought close to the Brewster angle θB (in the case of near point observation), image pickup signals obtained by picking up an optical image of the object 101 resulting from red internally scattered light, an optical image of the object 101 resulting from green internally scattered light, and an optical image of the object 101 resulting from blue internally scattered light are outputted to the processor 4.

Subsequently, the signal processing circuit 42 of the processor 4 generates a video signal by performing signal processing on the image pickup signals outputted from the endoscope 2 and outputs the video signal to the monitor 5 and the recording apparatus 6. Consequently, when the distance between the distal end face 221 of the distal end portion 21A and the surface of the object 101 is reduced until the incident angle θ is brought close to the Brewster angle θB (in the case of near point observation), images (P-polarized images) which make it easy to visually identify structures of fine blood vessels existing in inner part near the surface layer of the object 101 are displayed on the monitor 5 and recorded on the recording apparatus 6 based on the video signal.

By adjusting the distance between the distal end face 221 of the distal end portion 21A and the surface of the object 101 so as to bring the incident angle θ into coincidence with the Brewster angle θB, the present embodiment makes it possible to obtain images (P-polarized images) in which structures of fine blood vessels existing in inner part near the surface layer of the object 101 are visualized most clearly.

The present embodiment described above is configured to be able to obtain P-polarized images in near point observation without providing a polarizer on an incident light path of the return light from the object 101. Thus, in observing the structures of fine blood vessels existing in inner part near the surface layer of a living tissue, the present embodiment provides images which make it easy to visually identify the structures with improved brightness compared to the conventional technique.

Also, configuration conventionally used to obtain P-polarized images in near point observation includes, for example, a configuration in which a polarizer and an analyzer are arranged in a crossed-Nicols fashion on an emergent light path of illuminating light to the living tissue and on an incident light path of the return light of the illuminating light. However such a conventional configuration has a problem in that the configuration can provide only optical images dependent on the polarization characteristics of living tissue not only when observations are made by bringing the distal end face of the insertion portion close to the surface of the living tissue, but also when observations are made by spacing the distal end face of the insertion portion away from the surface of the living tissue, for example, as in the case of the far point observation described above. In contrast, the present embodiment described above is configured such that images (P-polarized images) based on optical images dependent on the polarization characteristics of living tissue can be obtained when observations are made by bringing the distal end face of the insertion portion close to the surface of the living tissue and that images (white light images) based on optical images substantially independent of the polarization characteristics of living tissue can be obtained when observations are made by spacing the distal end face of the insertion portion away from the surface of the living tissue. Consequently, the present embodiment described above makes it possible to obtain appropriate observation images according to the distance (observation distance) between the distal end face of the insertion portion and the surface of the living tissue in a simple manner without selectively using, for example, an apparatus configured to obtain P-polarized images and an apparatus configured to obtain white light images.

In observing the structures of fine blood vessels existing in inner part near the surface layer of a living tissue by near point observation, to improve viewability by removing surface-reflected light coming from the living tissue, conventionally a technique is used which involves, for example, filling a gap between the distal end face of the insertion portion and the surface of the living tissue with water before the observation. In contrast, without using the above-described technique, the present embodiment described above provides images which make it easy to visually identify the structures of fine blood vessels existing in inner part near the surface layer of the living tissue by the operation of bringing the distal end face of the insertion portion close to the living tissue to be observed. Consequently, the present embodiment described above eliminates the need for various operations (insertion and withdrawal of the insertion portion, replacement of water resulting from changes in a region to be observed, and so on) performed in the use of the above-described technique, and thereby shortens the time conventionally required for procedures and reduces burdens placed on the surgeon and the examinee during near point observation.

The present embodiment is not limited to the configuration in which the polarization direction of the illuminating light transmitted by the light guide 24 is aligned using the linear polarizer 211, and illuminating light aligned in a predetermined polarization direction in advance may be emitted through the illuminating window 213 using, for example, laser or the like as a light source.

Also, if the present embodiment described above is used in combination with a known vascular structure enhancement technique such as narrow band imaging and/or spectrum wavelength estimation, it can be made still easier to visually identify the structures of fine blood vessels existing in inner part near the surface layer of living tissue.

Second Embodiment

Figure 7:
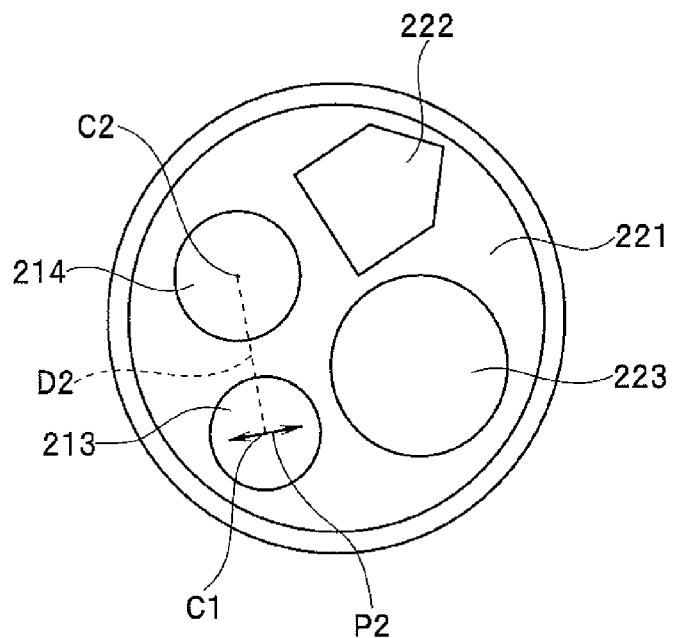
FIG. 7 is a diagram showing a component arrangement of principal part provided on a distal end face of a distal end portion of an endoscope according to a second embodiment.

FIG. 7 concerns a second embodiment of the present invention.

In the present embodiment, detailed description of part similar in configuration and the like to the first embodiment will be omitted, and part different in configuration and the like from the first embodiment will be mainly described.

In the present embodiment, the polarization characteristics of the linear polarizer 211 are changed so as to obtain a polarization direction (S-polarization) turned 90° from the predetermined polarization direction according to the first embodiment.

As a result of the change in the polarization characteristics of the linear polarizer 211, for example, as shown in FIG. 7, the illuminating window 213 and objective window 214 according to the present embodiment are configured such that in a plane (distal end face 221) which includes the optical axis of the illuminating window 213 (or the illumination optical system including the illuminating window 213) and the optical axis of the objective window 214 (or the objective optical system including the objective window 214), a line segment (broken line D2 in FIG. 7) connecting the two optical axes (center C1 and center C2 in FIG. 7) and a line segment (line segment P2 in FIG. 7) corresponding to the polarization direction of the illuminating light emitted through the illuminating window 213 and projected to the distal end face 221 are placed in such a positional relationship as to be at an angle of 90° (orthogonal) to each other.

The rest of the configuration can be similar to that of the first embodiment, and thus detailed description thereof will be omitted.

Next, operation of the present embodiment will be described.

First, the surgeon or the like connects various parts of the endoscope apparatus 1 as shown in FIG. 1 and powers on the various parts. Then, the surgeon or the like inserts the insertion portion 21 into the body of an examinee and brings the distal end portion 21A close to the object 101 in a desired observation region.

Consequently, illuminating light with substantially no polarization characteristics is emitted from the distal end portion 21A to illuminate the object 101. Then, internally scattered light produced by being transmitted through a surface of the object 101 and scattered in inner part near the surface layer and surface-reflected light produced by reflecting off the surface of the object 101 enter the objective window 214 as return light. Accordingly, on the image pickup surface of the image pickup device placed on the exit side of the second objective lens group 217, respective optical images of the object 101 are formed by the internally scattered light and the surface-reflected light and integrated into a single optical image.

That is, image pickup signals are obtained by picking up an optical image of the object 101 resulting from red internally scattered light and surface-reflected light, an optical image of the object 101 resulting from green internally scattered light and surface-reflected light, and an optical image of the object 101 resulting from blue internally scattered light and surface-reflected light, and the image pickup signals are outputted to the processor 4.

Subsequently, the signal processing circuit 42 of the processor 4 generates a video signal by performing signal processing on the image pickup signals outputted from the endoscope 2 and outputs the video signal to the monitor 5 and the recording apparatus 6. Consequently, images of substantially the same coloration (white light images) as in the case of observations made with the unaided eye are displayed on the monitor 5 and recorded on the recording apparatus 6 based on the video signal.

According to the present embodiment, in a plane (distal end face 221) which includes the optical axis of the illuminating window 213 and the optical axis of the objective window 214, a line segment (broken line D2 in FIG. 7) connecting the two optical axes (center C1 and center C2 in FIG. 7) and a line segment (line segment P2 in FIG. 7) corresponding to the polarization direction of the illuminating light emitted through the illuminating window 213 and projected to the distal end face 221 are placed in such a positional relationship as to be at an angle of 90° (orthogonal) to each other. That is, according to the present embodiment, since the illuminating light emitted to the object 101 through the illuminating window 213 has polarization characteristics of S-polarization whereby the illuminating light is at right angles to an incident plane of the illuminating light, angular characteristics of reflectance and transmittance indicated as "S-polarization imaging" in FIGS. 5A and 5B are applied.

In the case of far point observation shown in FIG. 4, the incident angle θ is relatively small. Therefore, in the case of far point observation, as shown in FIGS. 5A and 5B, both reflectance and transmittance of the illuminating light emitted through the illuminating window 213, as measured on the surface of the object 101, are substantially the same between when there are polarization characteristics and when there are not polarization characteristics as well as between different polarization directions. That is, in the case of far point observation, an intensity ratio between an optical image resulting from internally scattered light produced by being transmitted through the surface of the object 101 and scattered in inner part near the surface layer and an optical image resulting from surface-reflected light produced by reflecting off the surface of the object 101 is substantially the same between when the object 101 is illuminated by illuminating light having substantially no polarization characteristics and when the object 101 is illuminated by the illuminating light emitted through the illuminating window 213 according to the present embodiment.

Thus, according to the present embodiment, when there is a relatively large distance between the distal end face 221 of the distal end portion 21A and the surface of the object 101 (in the case of far point observation), observations can be made by watching substantially the same images as those obtained when the object 101 is illuminated by illuminating light having substantially no polarization characteristics.

On the other hand, as shown in FIG. 6, in the case of near point observation (when the distance between the distal end face 221 of the distal end portion 21A and the surface of the object 101 is reduced to a few mm to 10 mm), the incident angle θ can be set close to or above the Brewster angle θB.

When the object 101 is illuminated by illuminating light having polarization characteristics of S-polarization with the incident angle θ set close to or above the Brewster angle θB, surface-reflected light produced by reflecting off the surface of the object 101 enters the objective window 214 as return light having a higher intensity than when the object 101 is illuminated by illuminating light having substantially no polarization characteristics, as shown in FIG. 5A. On the other hand, when the object 101 is illuminated by illuminating light having polarization characteristics of S-polarization with the incident angle θ set close to or above the Brewster angle θB, intensity of internally scattered light produced by being scattered in inner part near the surface layer can be reduced compared to when the object 101 is illuminated by illuminating light having substantially no polarization characteristics, and thus little of the internally scattered light enters the objective window 214 as shown in FIG. 5B. Accordingly, on the image pickup surface of the image pickup device placed on the exit side of the second objective lens group 217, an optical image of the object 101 is produced by the surface-reflected light with the internally scattered light removed almost completely.

That is, when the distance between the distal end face 221 of the distal end portion 21A and the surface of the object 101 is reduced until the incident angle θ is close to or above the Brewster angle θB (in the case of near point observation), image pickup signals obtained by picking up an optical image of the object 101 resulting from red surface-reflected light, an optical image of the object 101 resulting from green surface-reflected light, and an optical image of the object 101 resulting from blue surface-reflected light are outputted to the processor 4.

Subsequently, the signal processing circuit 42 of the processor 4 generates a video signal by performing signal processing on the image pickup signals outputted from the endoscope 2 and outputs the video signal to the monitor 5 and the recording apparatus 6. Consequently, when the distance between the distal end face 221 of the distal end portion 21A and the surface of the object 101 is reduced until the incident angle θ is close to or above the Brewster angle θB (in the case of near point observation), images (S-polarized images) which make it easy to visually identify a fine concavo-convex structure existing on the surface of the object 101 are displayed on the monitor 5 and recorded on the recording apparatus 6 based on the video signal.

The present embodiment described above is configured such that images (S-polarized images) based on optical images dependent on the polarization characteristics of living tissue can be obtained when observations are made by bringing the distal end face of the insertion portion close to the surface of the living tissue and that images (white light images) based on optical images substantially independent of the polarization characteristics of living tissue can be obtained when observations are made by spacing the distal end face of the insertion portion away from the surface of the living tissue. Consequently, the present embodiment described above makes it possible to obtain appropriate observation images according to the distance (observation distance) between the distal end face of the insertion portion and the surface of the living tissue in a simple manner without selectively using, for example, an apparatus configured to obtain S-polarized images and an apparatus configured to obtain white light images.

In observing the fine concavo-convex structure existing on the surface of the living tissue by near point observation, to improve viewability by removing internally scattered light coming from the living tissue, conventionally a technique is used which involves, for example, spraying acetic acid, a pigment, or the like onto a target area before the observation. In contrast, without using the above-described technique, the present embodiment described above provides images which make it easy to visually identify the fine concavo-convex structure existing on the surface of the living tissue by the operation of bringing the distal end face of the insertion portion close to the living tissue to be observed. Consequently, the present embodiment described above eliminates the need for treatment such as agent spraying performed in the use of the above-described technique, and thereby shortens the time conventionally required for procedures and reduces burdens placed on the surgeon and examinee during near point observation.

Third Embodiment

Figure 8:
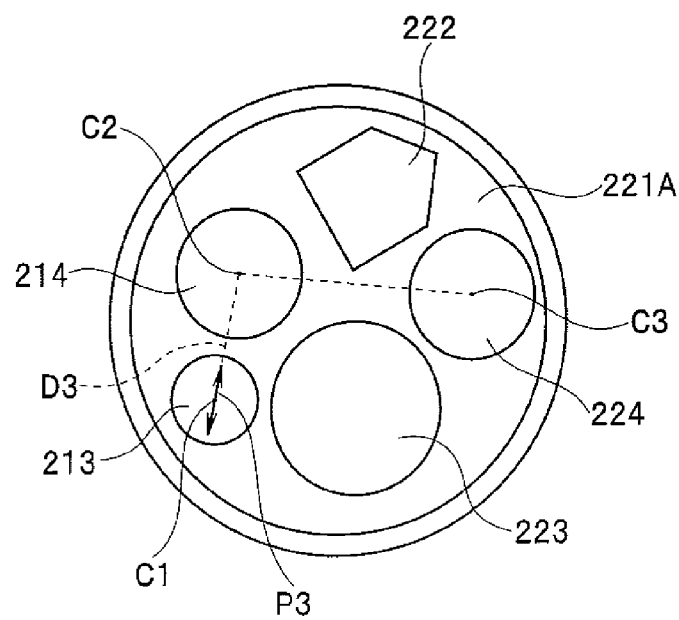
FIG. 8 is a diagram showing a component arrangement of principal part provided on a distal end face of a distal end portion of an endoscope according to a third embodiment.

FIG. 8 concerns a third embodiment of the present invention.

In the present embodiment, detailed description of part similar in configuration and the like to the first and second embodiments will be omitted, and part different in configuration and the like from the first and second embodiments will be mainly described.

As shown in FIG. 8, a distal end face 221A according to the present embodiment is provided with (an exit-side face of) an illuminating window 213, (an entrance-side face of) an objective window 214, a nozzle 222, a treatment instrument extrusion port 223, and (an exit-side face of) an illuminating window 224.

The illuminating window 224 is made of a convex lens and configured to be able to emit illuminating light without polarization characteristics to the object 101. Specifically, such a configuration can be implemented by selecting and adding an appropriate configuration to the configuration shown in the first embodiment, where possible configurations to select from involve, for example, providing a separate light guide intended to transmit illuminating light to the illuminating window 224, branching the light guide 24 to the side of the illuminating window 224, and placing a light source such as an LED adapted to give off RGB light (white color light) on the entrance side of the illuminating window 224.

As shown in FIG. 8, if it is assumed that the optical axis of the illuminating window 213 (or the illumination optical system including the illuminating window 213) passes through the center C1 of the illuminating window 213 and that the optical axis of the objective window 214 (or the objective optical system including the objective window 214) passes through the center C2 of the objective window 214, the illuminating window 213 and objective window 214 according to the present embodiment are placed in a positional relationship such that in a plane (distal end face 221A) which includes the optical axis of the illuminating window 213 and the optical axis of the objective window 214, a line segment (broken line D3 in FIG. 8) connecting the two optical axes (center C1 and center C2 in FIG. 8) is parallel to a line segment (line segment P3 in FIG. 8) corresponding to the polarization direction of the illuminating light emitted through the illuminating window 213 and projected to the distal end face 221A.

Furthermore, as shown in FIG. 8, if it is assumed that an optical axis of the illuminating window 224 (or the illumination optical system including the illuminating window 224) passes through a center C3 of the illuminating window 224, the illuminating window 213, objective window 214, and illuminating window 224 according to the present embodiment are placed in a positional relationship such that on the distal end face 221A, the distance between the center C1 and the center C2 is shorter than a distance between the center C2 and the center C3.

That is, on the distal end face 221A according to the present embodiment, the illuminating window 213 used to emit illuminating light whose polarization direction is aligned in a predetermined direction is placed at a position relatively close to the objective window 214 while the illuminating window 224 used to emit illuminating light without polarization characteristics is placed at a position relatively distant from the objective window 214.

The rest of the configuration can be similar to that of the first embodiment, and thus detailed description thereof will be omitted.

Next, operation of the present embodiment will be described.

First, the surgeon or the like connects various parts of the endoscope apparatus 1 as shown in FIG. 1 and powers on the various parts. Then, the surgeon or the like inserts the insertion portion 21 into the body of an examinee and brings the distal end portion 21A close to the object 101 in a desired observation region. In the present embodiment, it is assumed that illuminating lights are emitted simultaneously from the illuminating window 213 and the illuminating window 224.

On the other hand, according to the present embodiment, in the case of far point observation shown in FIG. 4, illuminating lights are emitted simultaneously from the illuminating window 213 and the illuminating window 224 in such a way, for example, that total quantity of light emitted from the illuminating window 224 is equal to or less than half the total quantity of light emitted from the illuminating window 213.

Thus, in the case of far point observation, when the quantities of the illuminating lights emitted simultaneously from the illuminating window 213 and the illuminating window 224 are adjusted as described above, the polarization characteristics of the illuminating light emitted through the illuminating window 213 are lessened, making it possible to illuminate the object 101 with the illuminating light whose polarization characteristics have been further reduced compared to the first embodiment. Accordingly, in the case of far point observation shown in FIG. 4, images of substantially the same coloration (white light images) as in the case of observations made with the unaided eye and of higher image quality than in the first embodiment are displayed on the monitor 5 and recorded on the recording apparatus 6.

On the other hand, as shown in FIG. 6, in the case of near point observation (when the distance between the distal end face 221A of the distal end portion 21A and the surface of the object 101 is reduced to a few mm to 10 mm), the incident angle θ can be set close to the Brewster angle θB. Therefore, in the case of near point observation, that local area of the object 101 which is closer to the objective window 214 is illuminated by the illuminating light emitted through the illuminating window 213 and having polarization characteristics of P-polarization. Also, in the case of near point observation, that local area of the object 101 which is distant from the objective window 214 is illuminated by the illuminating light emitted through the illuminating window 224 and having no polarization.

According to the present embodiment, as described above, the illuminating window 213 is placed close to the objective window 214 while the illuminating window 224 is spaced away from the objective window 214. Therefore, when near point observations are made using the configuration according to the present embodiment, whereas the internally scattered light produced by being scattered in inner part near the surface layer of the object 101 enters the objective window 214 as return light, the surface-reflected light produced by reflecting off the surface of the object 101 and reflected light of the illuminating light emitted to the object 101 through the illuminating window 224 hardly enter the objective window 214. Accordingly, on the image pickup surface of the image pickup device placed on the exit side of the second objective lens group 217, an optical image of the object 101 resulting from the internally scattered light is formed after the surface-reflected light and the reflected light of the illuminating light emitted to the object 101 through the illuminating window 224 are removed almost completely.

That is, when the distance between the distal end face 221A of the distal end portion 21A and the surface of the object 101 is reduced until the incident angle θ is close to the Brewster angle θB (in the case of near point observation), image pickup signals obtained by picking up an optical image of the object 101 resulting from red internally scattered light, an optical image of the object 101 resulting from green internally scattered light, and an optical image of the object 101 resulting from blue internally scattered light are outputted to the processor 4.

Subsequently, the signal processing circuit 42 of the processor 4 generates a video signal by performing signal processing on the image pickup signals outputted from the endoscope 2 and outputs the video signal to the monitor 5 and the recording apparatus 6. Consequently, when the distance between the distal end face 221A of the distal end portion 21A and the surface of the object 101 is reduced until the incident angle θ is close to the Brewster angle θB (in the case of near point observation), images (P-polarized images) which make it easy to visually identify structures of fine blood vessels existing in inner part near the surface layer of the object 101 are displayed on the monitor 5 and recorded on the recording apparatus 6 based on the video signal.

In addition to providing advantages similar to those described in the first embodiment, the present embodiment described above further provides the advantage of improving image quality of observation images obtained during far point observation.

Fourth Embodiment

Figure 9:
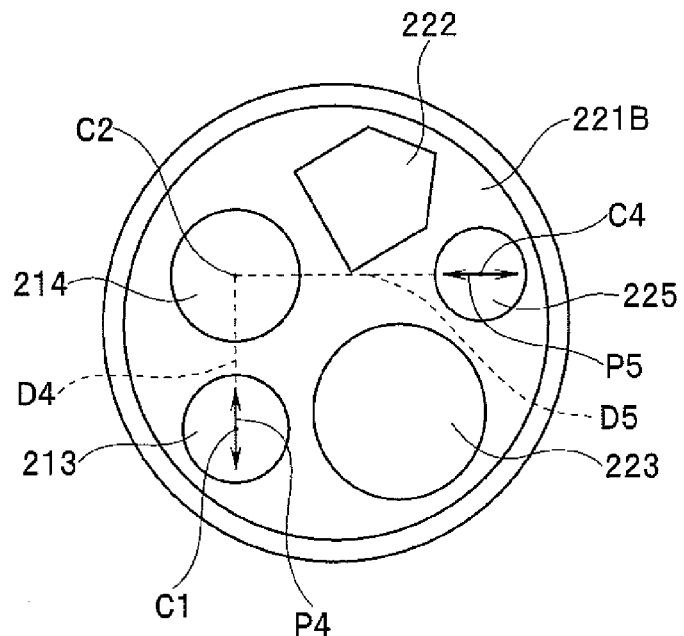
FIG. 9 is a diagram showing a component arrangement of principal part provided on a distal end face of a distal end portion of an endoscope according to a fourth embodiment.
Figure 10:
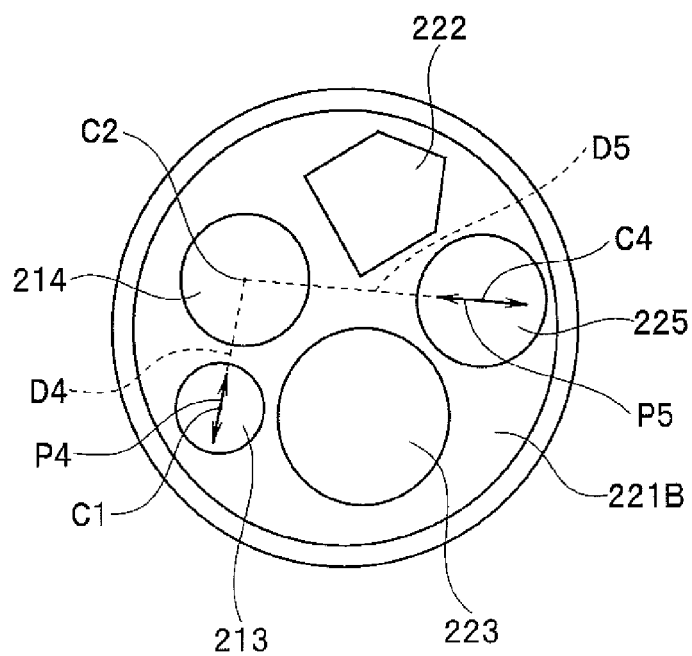
FIG. 10 is a diagram showing a component arrangement of principal part provided on a distal end face of a distal end portion of an endoscope according to a variation of the fourth embodiment.

FIGS. 9 and 10 concern a fourth embodiment of the present invention.

In the present embodiment, detailed description of part similar in configuration and the like to the first to third embodiments will be omitted, and part different in configuration and the like from the first to third embodiments will be mainly described.

As shown in FIG. 9, a distal end face 221B according to the present embodiment is provided with (an exit-side face of) an illuminating window 213, (an entrance-side face of) an objective window 214, a nozzle 222, a treatment instrument extrusion port 223, and (an exit-side face of) an illuminating window 225.

The illuminating window 225 is made of a convex lens and configured to be able to emit illuminating light to the object 101 in a polarization direction turned 90° from the polarization direction of the illuminating light emitted through the illuminating window 213. Specifically, such a configuration can be implemented, for example, by combining two configurations shown in the first embodiment.

As shown in FIG. 9, if it is assumed that the optical axis of the illuminating window 213 (or the illumination optical system including the illuminating window 213) passes through the center C1 of the illuminating window 213 and that the optical axis of the objective window 214 (or the objective optical system including the objective window 214) passes through the center C2 of the objective window 214, the illuminating window 213 and objective window 214 according to the present embodiment are placed in a positional relationship such that in a plane (distal end face 221B) which includes the optical axis of the illuminating window 213 and the optical axis of the objective window 214, a line segment (broken line D4 in FIG. 9) connecting the two optical axes (center C1 and center C2 in FIG. 9) is parallel to a line segment (line segment P4 in FIG. 9) corresponding to the polarization direction of the illuminating light emitted through the illuminating window 213 and projected to the distal end face 221B. With this configuration, illuminating light having polarization characteristics of P-polarization is emitted through the illuminating window 213 as in the case of the first embodiment.

Also, as shown in FIG. 9, if it is assumed that the optical axis of the illuminating window 225 (or the illumination optical system including the illuminating window 225) passes through a center C4 of the illuminating window 225, the illuminating window 225 and objective window 214 according to the present embodiment are placed in a positional relationship such that in a plane (distal end face 221B) which includes the optical axis of the objective window 214 and the optical axis of the illuminating window 225, a line segment (broken line D5 in FIG. 9) connecting the two optical axes (center C2 and center C4 in FIG. 9) is parallel to a line segment (line segment P5 in FIG. 9) corresponding to the polarization direction of the illuminating light emitted through the illuminating window 225 and projected to the distal end face 221B. With this configuration, illuminating light having polarization characteristics of P-polarization is emitted through the illuminating window 225.

Furthermore, as shown in FIG. 9, the illuminating window 213, objective window 214, and illuminating window 225 according to the present embodiment are placed in a positional relationship such that on the distal end face 221B, the distance between the center C1 and the center C2 is shorter than a distance between the center C2 and the center C4 while the line segment connecting the center C1 and the center C2 (broken line D4 in FIG. 9) and the line segment connecting the center C2 and the center C4 (broken line D5 in FIG. 9) are placed in such a positional relationship as to be at an angle of 90° (orthogonal) to each other.

That is, on the distal end face 221B according to the present embodiment, the illuminating window 213 used to emit illuminating light whose polarization direction is aligned in a predetermined direction is placed at a position relatively close to the objective window 214, and the illuminating window 225 used to emit illuminating light in a polarization direction turned 90° from the predetermined direction is placed at a position relatively distant from the objective window 214.

The rest of the configuration can be similar to that of the first embodiment, and thus detailed description thereof will be omitted.

Next, operation of the present embodiment will be described.

First, the surgeon or the like connects various parts of the endoscope apparatus 1 as shown in FIG. 1 and powers on the various parts. Then, the surgeon or the like inserts the insertion portion 21 into the body of an examinee and brings the distal end portion 21A close to the object 101 in a desired observation region. In the present embodiment, it is assumed that illuminating lights are emitted simultaneously from the illuminating window 213 and the illuminating window 225.

On the other hand, according to the present embodiment, in the case of far point observation shown in FIG. 4, illuminating lights are emitted simultaneously from the illuminating window 213 and the illuminating window 225 in such a way, for example, that total quantity of light emitted from one of the illuminating windows will fall within a range of −50% to +50% of the total quantity of light emitted from the other of the illuminating windows. (Consequently, the illuminating lights are emitted such that if the total quantity of light emitted from the one illuminating window is taken as 100, the total quantity of light emitted from the other illuminating window will fall within a range of 50 to 150.)

Thus, in the case of far point observation, when the quantities of the illuminating lights emitted simultaneously from the illuminating window 213 and the illuminating window 225 are adjusted as described above, the polarization characteristics of the illuminating lights emitted through the two illuminating windows are both lessened, making it possible to illuminate the object 101 with the illuminating light whose polarization characteristics have been further reduced compared to the first and third embodiments. Accordingly, in the case of far point observation shown in FIG. 4, images of substantially the same coloration (white light images) as in the case of observations made with the unaided eye and of higher image quality than in the first and third embodiments are displayed on the monitor 5 and recorded on the recording apparatus 6.

On the other hand, as shown in FIG. 6, in the case of near point observation (when the distance between the distal end face 221B of the distal end portion 21A and the surface of the object 101 is reduced to a few mm to 10 mm), the incident angle θ can be set close to the Brewster angle θB. Therefore, in the case of near point observation, that local area of the object 101 which is closer to the objective window 214 is illuminated by the P-polarized illuminating lights emitted through the illuminating window 213 and the illuminating window 225.

When near point observations are made using the configuration according to the present embodiment, whereas the internally scattered light produced by being scattered in inner part near the surface layer of the object 101 enters the objective window 214 as return light, little (or none) of the surface-reflected light produced by reflecting off the surface of the object 101 enters the objective window 214. Accordingly, on the image pickup surface of the image pickup device placed on the exit side of the second objective lens group 217, an optical image of the object 101 resulting from the internally scattered light is formed with the surface-reflected light removed almost completely (or completely).

That is, when the distance between the distal end face 221B of the distal end portion 21A and the surface of the object 101 is reduced until the incident angle θ is close to the Brewster angle θB (in the case of near point observation), image pickup signals obtained by picking up an optical image of the object 101 resulting from red internally scattered light, an optical image of the object 101 resulting from green internally scattered light, and an optical image of the object 101 resulting from blue internally scattered light are outputted to the processor 4.

Subsequently, the signal processing circuit 42 of the processor 4 generates a video signal by performing signal processing on the image pickup signals outputted from the endoscope 2 and outputs the video signal to the monitor 5 and the recording apparatus 6. Consequently, when the distance between the distal end face 221B of the distal end portion 21A and the surface of the object 101 is reduced until the incident angle θ is close to the Brewster angle θB (in the case of near point observation), images (P-polarized images) which make it easy to visually identify structures of fine blood vessels existing in inner part near the surface layer of the object 101 are displayed on the monitor 5 and recorded on the recording apparatus 6 based on the video signal.

Incidentally, the present embodiment is not limited to the configuration described above. For example, the polarization direction of the illuminating light emitted through the illuminating window 213 and the polarization direction of the illuminating light emitted through the illuminating window 225 may be each turned 90° from the configuration described above. This will make it possible to obtain images (white light images) such as described above in the case of far point observation and obtain images (S-polarized images) which make it easy to visually identify a fine concavo-convex structure existing on the surface of the object 101 as with the second embodiment in the case of near point observation.

According to the present embodiment, as long as the quantities of the illuminating lights emitted simultaneously from the illuminating window 213 and the illuminating window 225 are adjusted as described above, image quality of the images obtained by far point observation can be maintained at or above a predetermined level. Therefore, on the distal end face 221B according to the present embodiment, the line segment connecting the center C1 and the center C2 (broken line D4 in FIG. 10) and the line segment connecting the center C2 and the center C4 (broken line D5 in FIG. 10) may be placed in such a positional relationship as to be at an angle other than 90° (slightly deviated from 90°), for example, as shown in FIG. 10.

In addition to providing advantages similar to those described in the first embodiment, the present embodiment described above further provides the advantage of improving brightness of observation images obtained during near point observation.

Fifth Embodiment

Figure 11:
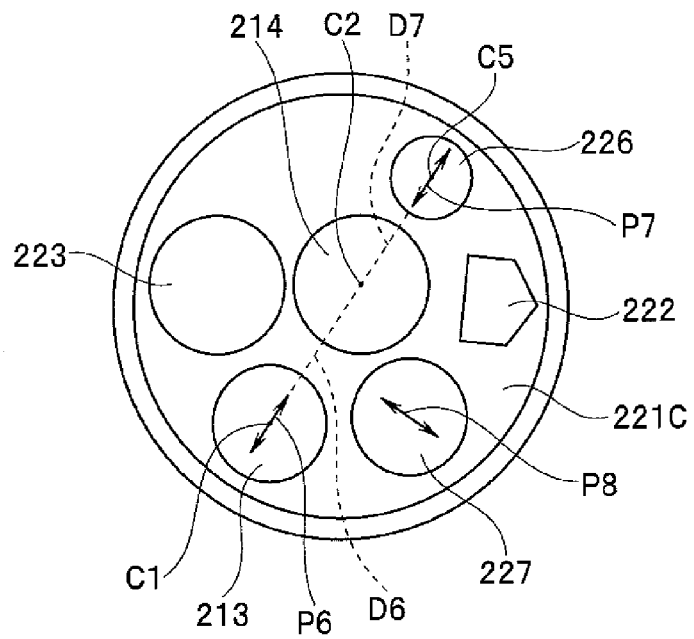
FIG. 11 is a diagram showing a component arrangement of principal part provided on a distal end face of a distal end portion of an endoscope according to a fifth embodiment.

FIG. 11 concerns a fifth embodiment of the present invention.

In the present embodiment, detailed description of part similar in configuration and the like to the first to fourth embodiments will be omitted, and part different in configuration and the like from the first to fourth embodiments will be mainly described.

As shown in FIG. 11, a distal end face 221C according to the present embodiment is provided with (an exit-side face of) an illuminating window 213, (an entrance-side face of) an objective window 214, a nozzle 222, a treatment instrument extrusion port 223, an illuminating window 226, and an objective window 227.

The illuminating window 226 is made of a convex lens and configured to be able to emit illuminating light to the object 101 in the same polarization direction (P-polarization) as the polarization direction of the illuminating light emitted through the illuminating window 213. Specifically, such a configuration can be implemented, for example, using the configuration shown in the first embodiment.

As shown in FIG. 11, if it is assumed that the optical axis of the illuminating window 213 (or the illumination optical system including the illuminating window 213) passes through the center C1 of the illuminating window 213 and that the optical axis of the objective window 214 (or the objective optical system including the objective window 214) passes through the center C2 of the objective window 214, the illuminating window 213 and objective window 214 according to the present embodiment are placed in a positional relationship such that in a plane (distal end face 221C) which includes the optical axis of the illuminating window 213 and the optical axis of the objective window 214, a line segment (broken line D6 in FIG. 11) connecting the two optical axes (center C1 and center C2 in FIG. 11) is parallel to a line segment (line segment P6 in FIG. 11) corresponding to the polarization direction of the illuminating light emitted through the illuminating window 213 and projected to the distal end face 221C.

Also, as shown in FIG. 11, if it is assumed that an optical axis of the illuminating window 226 (or the illumination optical system including the illuminating window 226) passes through a center C5 of the illuminating window 226, the illuminating window 226 and objective window 214 according to the present embodiment are placed in a positional relationship such that in a plane (distal end face 221C) which includes the optical axis of the objective window 214 and the optical axis of the illuminating window 226, a line segment (broken line D7 in FIG. 11) connecting the two optical axes (center C2 and center C5 in FIG. 11) is parallel to a line segment (line segment P7 in FIG. 11) corresponding to the polarization direction of the illuminating light emitted through the illuminating window 226 and projected to the distal end face 221C.

On an exit side of the objective window 227 made of a concave lens, multiple objective lens groups and an objective diaphragm are provided, creating a component arrangement similar to the one described in FIG. 2 according to the first embodiment, and an analyzer (not shown) is provided in a crossed-Nicols manner with respect to the polarization direction of the linear polarizer 211. Incidentally, the polarization direction of the analyzer corresponds, for example, to the direction of a line segment P8 in FIG. 11.

Furthermore, an image pickup device (not shown) capable of picking up optical images corresponding to light passing through the analyzer and outputting image pickup signals to the processor 4 is provided on the exit side of the objective window 227.

The rest of the configuration can be similar to that of the first embodiment, and thus detailed description thereof will be omitted.

Next, operation of the present embodiment will be described.

First, the surgeon or the like connects various parts of the endoscope apparatus 1 as shown in FIG. 1 and powers on the various parts. Then, the surgeon or the like inserts the insertion portion 21 into the body of an examinee and brings the distal end portion 21A close to the object 101 in a desired observation region. In the present embodiment, it is assumed that illuminating lights are emitted simultaneously from the illuminating window 213 and the illuminating window 226.

In the case of far point observation shown in FIG. 4, as described in the first embodiment, both reflectance and transmittance of the illuminating light emitted from the distal end portion 21A, as measured on the surface of the object 101, are substantially the same between when there are polarization characteristics and when there are not polarization characteristics as well as between different polarization directions. Consequently, as in the case of the first embodiment, an optical image of the object 101 substantially equivalent to an image obtained when the object 101 is illuminated by illuminating light having substantially no polarization characteristics is formed on the image pickup surface of the image pickup device placed on the exit side of the second objective lens group 217. On the other hand, an optical image corresponding to return light passing through the above-described analyzer is formed on the image pickup surface of the image pickup device placed on the exit side of the objective window 227.

In the case of near point observation, since the object 101 is illuminated by P-polarized illuminating light, the internally scattered light produced by being scattered in inner part near the surface layer of the object 101 enters the objective window 214 and the objective window 227 as return light. Accordingly, an optical image of the object 101 resulting from the internally scattered light is formed on the image pickup surface of the image pickup device placed on the exit side of the second objective lens group 217. On the other hand, an optical image of the object 101 resulting from the internally scattered light passing through the above-described analyzer is formed on the image pickup surface of the image pickup device placed on the exit side of the objective window 227.

The signal processing circuit 42 of the processor 4 generates video signals by performing signal processing on the image pickup signals outputted, respectively, from the image pickup device placed on the exit side of the second objective lens group 217 and the image pickup device placed on the exit side of the objective window 227, and outputs the video signals to the monitor 5 and the recording apparatus 6. Consequently, in the case of far point observation, images of substantially the same coloration (white light images) as in the case of observations made with the unaided eye as well as images which make it easy to identify a lesion such as cancer existing in inner part near the surface layer of the object 101 are displayed on the monitor 5 and recorded on the recording apparatus 6 based on the video signals. Also, in the case of near point observation, images (P-polarized images) which make it easy to visually identify structures of fine blood vessels existing in inner part near the surface layer of the object 101 as well as images which make it easy to identify a lesion such as cancer existing in inner part near the surface layer of the object 101 are displayed on the monitor 5 and recorded on the recording apparatus 6 based on the video signals. The two types of images may be either generated separately or combined by an image combination process as appropriate.

In addition to providing advantages similar to those described in the first embodiment, the present embodiment described above further provides the advantage of making a large volume of useful information available when carrying out a diagnosis based on findings obtained by far to near point observations.

Sixth Embodiment

Figure 12:
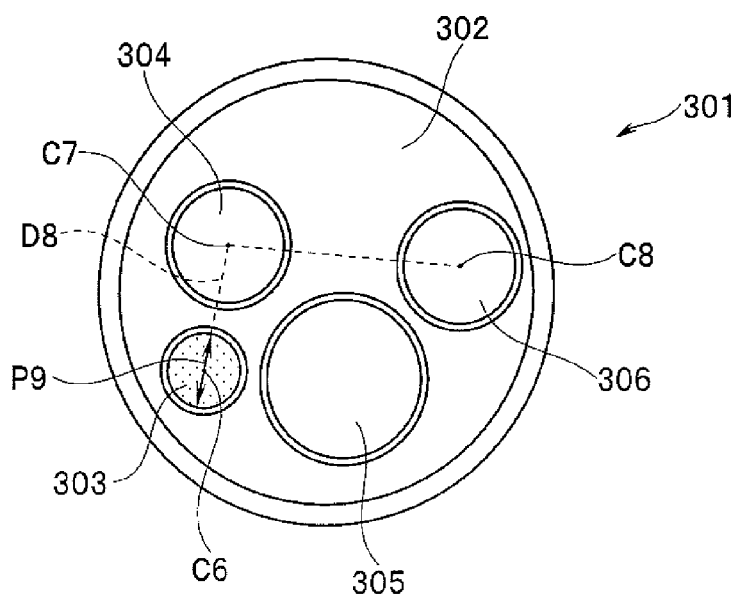
FIG. 12 is a diagram showing a component arrangement of principal part provided on a bottom face of a cap according to a sixth embodiment.
Figure 13:
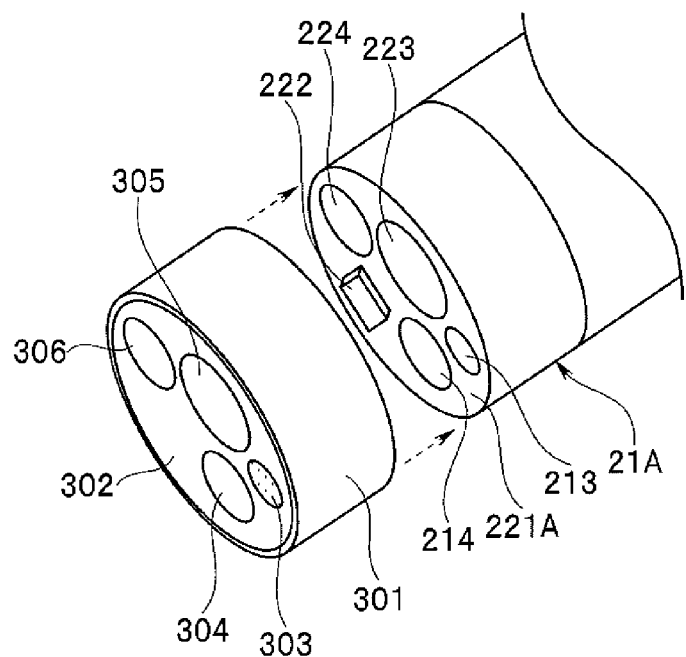
FIG. 13 is a diagram showing a state existing before the cap shown in FIG. 12 is attached to a distal end portion of an endoscope.
Figure 14:
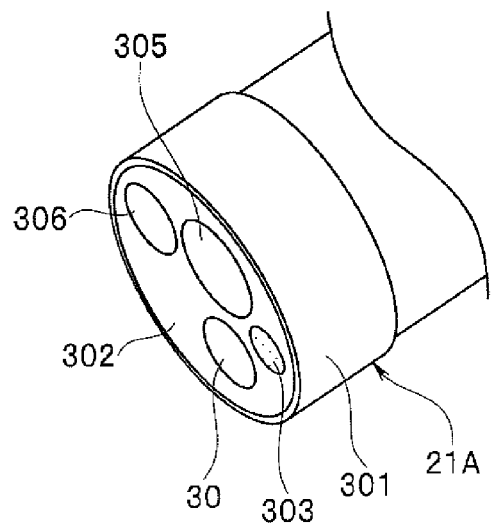
FIG. 14 is a diagram showing a state existing after the cap shown in FIG. 12 is attached to the distal end portion of the endoscope.

FIGS. 12 to 14 concern a sixth embodiment of the present invention.

In the present embodiment, detailed description of part similar in configuration and the like to the first to fifth embodiments will be omitted, and part different in configuration and the like from the first to fifth embodiments will be mainly described. The present embodiment will be described by taking as an example an endoscope 2 in which the distal end face 221A according to the third embodiment is provided in the distal end portion 21A and the linear polarizer 211 is not provided on the exit side of the light guide 24.

A cap 301 according to the present embodiment is shaped to be able to be inserted and fitted in the distal end portion 21A. Specifically, as shown in FIGS. 12 to 14, the cap 301 according to the present embodiment has a substantially cylindrical shape with a bottom face 302 placed facing the distal end face 221A when the cap 301 is attached to the distal end portion 21A.

As shown, for example, in FIG. 12, an illuminating window 303, an objective window 304, a treatment instrument window 305, and an illuminating window 306 are provided in the bottom face 302 of the cap 301, where the illuminating window 303 is formed to conform to the shape of the illuminating window 213, the objective window 304 is formed to conform to the shape of the objective window 214, the treatment instrument window 305 is formed to conform to the shape of the treatment instrument extrusion port 223, and the illuminating window 306 is formed to conform to the shape of the illuminating window 224.

The illuminating window 303 includes a polarizing filter capable of aligning illuminating light passing through the illuminating window 213 in a predetermined polarization direction (P-polarization). Consequently, the illuminating light which has passed through the illuminating window 303 is emitted to the object 101 as illuminating light of the predetermined polarization direction (P-polarization).

The objective window 304 is configured to be able to emit the return light from the object 101 to the objective window 214 when the cap 301 is inserted and fitted in the distal end portion 21A.

The illuminating window 306 is configured to be able to emit the illuminating light which has passed through the illuminating window 224 to the object 101 when the cap 301 is inserted and fitted in the distal end portion 21A.

The objective window 304 and illuminating window 306 according to the present embodiment may be made of an optical member such as a transparent plate glass or formed by producing a hole in the bottom face 302.

On the other hand, the parts provided in the bottom face 302 of the cap 301 are arranged so as to correspond in positional relationships to the parts provided in the distal end face 221A. That is, as shown in FIG. 12, if it is assumed that the optical axis of the illuminating window 213 passes through a center C6 of the illuminating window 303, and that the optical axis of the objective window 214 passes through a center C7 of the objective window 304, the illuminating window 303 and objective window 304 according to the present embodiment are placed in a positional relationship such that in a plane (bottom face 302) which includes the optical axis of the illuminating window 213 and the optical axis of the objective window 214, a line segment (broken line D8 in FIG. 12) connecting the two optical axes (center C6 and center C7 in FIG. 12) is parallel to a line segment (line segment P9 in FIG. 12) corresponding to the polarization direction of the illuminating light emitted through the illuminating window 213 and the illuminating window 303 and projected to the bottom face 302.

Furthermore, as shown in FIG. 12, if it is assumed that the optical axis of the illuminating window 224 passes through a center C8 of the illuminating window 306, the illuminating window 303, objective window 304, and illuminating window 306 according to the present embodiment are placed in a positional relationship such that on the bottom face 302, a distance between the center C6 and the center C7 is shorter than a distance between the center C7 and the center C8.

That is, on the bottom face 302 according to the present embodiment, the illuminating window 303 used to emit illuminating light whose polarization direction is aligned in a predetermined direction is placed at a position relatively close to the objective window 304 while the illuminating window 306 used to emit illuminating light without polarization characteristics is placed at a position relatively distant from the objective window 304.

The rest of the configuration can be similar to that of the first or third embodiment, and thus detailed description thereof will be omitted.

Next, operation of the present embodiment will be described.

First, the surgeon or the like connects various parts of the endoscope apparatus 1 as shown in FIG. 1 and powers on the various parts. In the meantime, the surgeon or the like inserts and fits the cap 301 in the distal end portion 21A by bringing the positional relationships among the parts provided in the bottom face 302 of the cap 301 into correspondence with the positional relationships among the parts provided in the distal end face 221A, as shown in FIG. 13. As a result of this operation, the cap 301 is attached to the distal end portion 21A, for example, in a state shown in FIG. 14.

Then, with the cap 301 attached to the distal end portion 21A, the surgeon or the like inserts the insertion portion 21 into the body of an examinee and brings the distal end portion 21A close to the object 101 in a desired observation region. According to the present embodiment, it is assumed that illuminating lights are emitted simultaneously from the illuminating window 213 and the illuminating window 224.

On the other hand, according to the present embodiment, in the case of far point observation shown in FIG. 4, illuminating lights are emitted simultaneously from the illuminating window 213 and the illuminating window 224 in such a way, for example, that total quantity of light emitted from the illuminating window 213 is equal to or less than half the total quantity of light emitted from the illuminating window 224.

Thus, in the case of far point observation, when the quantities of the illuminating lights emitted simultaneously from the illuminating window 213 and the illuminating window 224 are adjusted as described above, the polarization characteristics of the illuminating light emitted through the illuminating window 303 are lessened, making it possible to illuminate the object 101 with substantially the same illuminating light as in the third embodiment. Accordingly, in the case of far point observation shown in FIG. 4, images of substantially the same coloration (white light images) as in the case of observations made with the unaided eye and of substantially the same quality as in the third embodiment are displayed on the monitor 5 and recorded on the recording apparatus 6.

On the other hand, as shown in FIG. 6, in the case of near point observation (when the distance between the bottom face 302 of the cap 301 and the surface of the object 101 is reduced to a few mm to 10 mm), the incident angle θ can be set close to the Brewster angle θB. Therefore, in the case of near point observation, that local area of the object 101 which is closer to the objective window 304 is illuminated by the illuminating light emitted through the illuminating window 303 and having polarization characteristics of P-polarization. Also, in the case of near point observation, that local area of the object 101 which is distant from the objective window 304 is illuminated by the illuminating light emitted through the illuminating window 306 and having no polarization.

According to the present embodiment, as described above, the illuminating window 303 is placed close to the objective window 304 while the illuminating window 306 is spaced away from the objective window 304. Therefore, when near point observations are made using the configuration according to the present embodiment, whereas the internally scattered light produced by being scattered in inner part near the surface layer of the object 101 enters the objective window 304 as return light, the surface-reflected light produced by reflecting off the surface of the object 101 and reflected light of the illuminating light emitted to the object 101 through the illuminating window 306 hardly enter the objective window 304. Accordingly, on the image pickup surface of the image pickup device placed on the exit side of the second objective lens group 217, an optical image of the object 101 resulting from the internally scattered light is formed after the surface-reflected light and the reflected light of the illuminating light emitted to the object 101 through the illuminating window 306 are removed almost completely.

That is, when the distance between the bottom face 302 of the cap 301 and the surface of the object 101 is reduced until the incident angle θ is close to the Brewster angle θB (in the case of near point observation), image pickup signals obtained by picking up an optical image of the object 101 resulting from red internally scattered light, an optical image of the object 101 resulting from green internally scattered light, and an optical image of the object 101 resulting from blue internally scattered light are outputted to the processor 4.

Subsequently, the signal processing circuit 42 of the processor 4 generates a video signal by performing signal processing on the image pickup signals outputted from the endoscope 2 and outputs the video signal to the monitor 5 and the recording apparatus 6. Consequently, when the distance between the bottom face 302 of the cap 301 and the surface of the object 101 is reduced until the incident angle θ is close to the Brewster angle θB (in the case of near point observation), images (P-polarized images) which make it easy to visually identify structures of fine blood vessels existing in inner part near the surface layer of the object 101 are displayed on the monitor 5 and recorded on the recording apparatus 6 based on the video signal.

Even when the endoscope used does not have a polarizer provided either on an emergent light path of the illuminating light to the object or on the incident light path of the return light of the illuminating light, the present embodiment described above provides images which make it easy to visually identify the structures of fine blood vessels existing in inner part near the surface layer of the living tissue, and consequently provides advantages substantially similar to those described in the third embodiment.

Incidentally, in the present embodiment, to provide images which make it easy to visually identify the fine concavo-convex structure existing on the surface of the living tissue, the configuration of the second embodiment may be applied to the positional relationship related to the arrangement of the illuminating window 303 and the objective window 304. Specifically, the illuminating window 303 and objective window 304 according to the present embodiment may be configured such that in a plane (bottom face 302) which includes the optical axis of the illuminating window 213 and the optical axis of the objective window 214, a line segment (broken line D8 in FIG. 12) connecting the two optical axes (center C6 and center C7 in FIG. 12) and a line segment (line segment P9 in FIG. 12) corresponding to the polarization direction of the illuminating light emitted through the illuminating window 213 and the illuminating window 303 and projected to the bottom face 302 are placed in such a positional relationship as to be at an angle of 90° (orthogonal) to each other.

It should be noted that the present invention is not limited to the embodiments described above, and needless to say that various alterations and applications are possible without departing from the spirit of the invention.

What is claimed is:

1. An endoscope comprising:
a first illumination optical system configured to include a polarizing element between a light source and an illuminating window and emit illuminating light in a first linear polarization direction to an object from the illuminating window;
a first objective optical system configured to allow return light from the object illuminated by the illuminating light to enter through an objective window provided in a distal end face of an insertion portion; and
an image pickup device configured to receive an image formed by the first objective optical system;
wherein the first illumination optical system and the first objective optical system are placed in a positional relationship such that on the distal end face, a line segment connecting an optical axis of the first illumination optical system and an optical axis of the first objective optical system is parallel or perpendicular to a polarization direction which results when the illuminating light emitted from the first illumination optical system is projected to the distal end face, and
no polarizing element is provided between the object and the image pickup device.

2. The endoscope according to claim 1, further comprising a second illumination optical system configured to emit illuminating light to the object from the distal end face, wherein on the distal end face, the first illumination optical system is placed at a position relatively close to the first objective optical system and the second illumination optical system is placed at a position relatively distant from the first objective optical system.

3. The endoscope according to claim 1, further comprising a second illumination optical system configured to emit illuminating light to the object from the distal end face,
wherein the second illumination optical system is configured to emit illuminating light in a second linear polarization direction to the object from the distal end face; and
the second illumination optical system and the first objective optical system are placed in a positional relationship such that on the distal end face, a line segment connecting an optical axis of the second illumination optical system and the optical axis of the first objective optical system is parallel or perpendicular to a polarization direction which results when the illuminating light emitted from the second illumination optical system is projected to the distal end face.

4. The endoscope according to claim 3, wherein the second linear polarization direction corresponds to a polarization direction turned 90° from the first linear polarization direction.

5. The endoscope according to claim 3, wherein the first illumination optical system, the second illumination optical system, and the first objective optical system are placed in a positional relationship such that on the distal end face, the line segment connecting the optical axis of the first illumination optical system and the optical axis of the first objective optical system and the line segment connecting the optical axis of the second illumination optical system and the optical axis of the first objective optical system are orthogonal to each other.

6. The endoscope according to claim 1, further comprising a second objective optical system configured to allow return light from the object to enter through the distal end face.

7. An endoscope apparatus comprising:
the endoscope according to claim 1;
a light source apparatus adapted to supply the endoscope with light having no polarization characteristics; and
a processor adapted to generate an observation image according to an optical image of the object obtained by the endoscope.

\* \* \* \* \*